US 6,589,285 B2
(12) United States Patent
Penenberg

(10) Patent No.: US 6,589,285 B2
(45) Date of Patent: Jul. 8, 2003

(54) APPARATUS FOR, AND METHOD OF, PROVIDING HIP PROSTHESIS IMPLANTATION

(75) Inventor: Brad L. Penenberg, Los Angeles, CA (US)

(73) Assignee: Centerpulse Orthopedics Inc., Austin, TX (US)

( * ) Notice: Subject to any disclaimer, the term of this patent is extended or adjusted under 35 U.S.C. 154(b) by 0 days.

(21) Appl. No.: 09/996,466

(22) Filed: Nov. 20, 2001

(65) Prior Publication Data

US 2003/0097135 A1 May 22, 2003

(51) Int. Cl.[7] .............. A61E 2/72; A61F 5/00; A61F 2/00
(52) U.S. Cl. ............... 623/23.26; 623/23.39; 623/23.15; 623/23.36; 606/86; 606/95
(58) Field of Search ............ 623/16.11, 18.11, 623/23.11, 22.4, 22.11, 23.15, 23.26, 23.28, 23.36, 37; 606/86, 92, 95, 89, 99, 94, 102, 100

(56) References Cited

U.S. PATENT DOCUMENTS

| 5,470,336 | A | * | 11/1995 | Ling et al. | 606/105 |
|---|---|---|---|---|---|
| 5,665,121 | A | * | 9/1997 | Gie et al. | 128/898 |
| 5,788,704 | A | * | 8/1998 | Timperley | 606/95 |
| 5,800,437 | A | * | 9/1998 | Gustilo et al. | 606/86 |
| 5,910,172 | A | * | 6/1999 | Penenberg | 623/23.21 |
| 5,989,259 | A | * | 11/1999 | Penenberg et al. | 606/99 |
| 5,997,581 | A | * | 12/1999 | Khalili | 623/23.48 |
| 6,142,998 | A | * | 11/2000 | Smith et al. | 606/86 |
| 6,143,030 | A | * | 11/2000 | Schroder | 623/16.11 |
| 6,217,583 | B1 | * | 4/2001 | Storer | 606/92 |
| 6,270,502 | B1 | * | 8/2001 | Stulberg | 606/86 |
| 6,309,395 | B1 | * | 10/2001 | Smith et al. | 606/92 |
| 6,355,069 | B1 | * | 3/2002 | DeCarlo et al. | 623/23.26 |

* cited by examiner

Primary Examiner—Pedro Philogene
Assistant Examiner—D. Austin Bonderer
(74) Attorney, Agent, or Firm—Kenneth S. Barrow

(57) ABSTRACT

Surface irregularities are removed from the inner wall of a femur cavity, preferably tapered. A tamp having an opening and a socket is disposed in the cavity. The tamp may be one of a plurality of tamps each having a different length for the opening. A guide, one of a plurality, fits snugly in the opening. The guide has a collar which cooperates with the tamp socket to limit the movement of the guide into the tamp. A working portion of each guide below the intermediate position has a bulbous shape which is tapered in accordance with the femur taper. Bone fragments between the guide working portion and the femur inner wall are packed against the inner wall when the tamp and the guide are driven into the femur cavity. Numerals on the guide adjacent a slot in the tamp indicate the disposition of the guide in the tamp. Guides with working portions of progressively increasing lengths are disposed sequentially in progressive ones of the tamps to pack fragments at an increasing height in the femur cavity against the cavity inner wall. When the last one of the tamps and the last one of the guides have been removed from the cavity, a prosthesis having dimensions slightly less than the femur cavity dimensions is disposed in the cavity. A binder disposed in the cavity in the space between the inner wall of the femur cavity and the prosthesis binds the prosthesis to the femur. In one embodiment, the tamp socket is an opening and the guide collar fits into the tamp opening to limit the movement of the guide into the tamp. In a modification, the tamp socket is disposed in a press fit on the guide collar to limit the movement of the guide into the tamp.

23 Claims, 6 Drawing Sheets

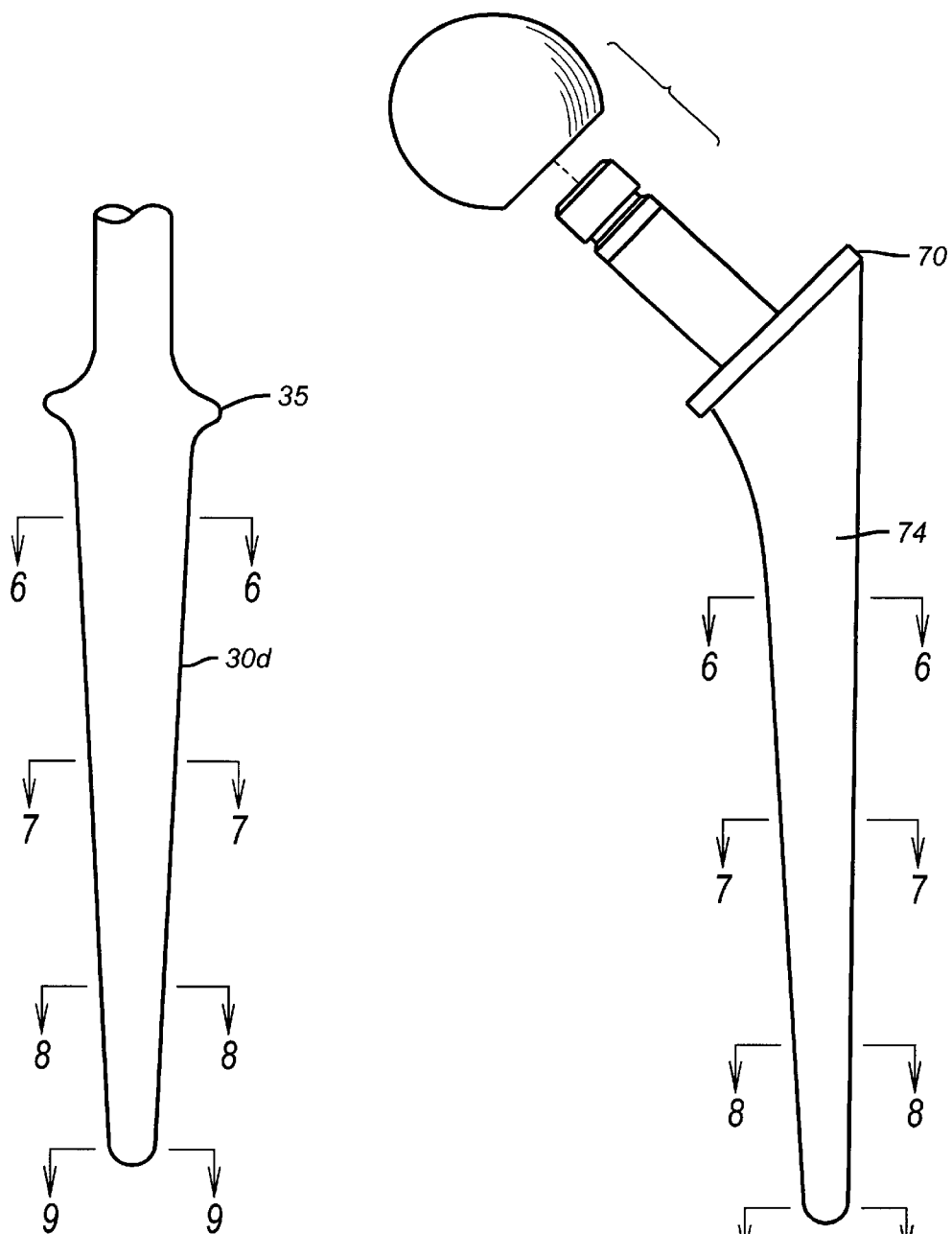
FIG. 4  FIG. 5
   
FIG. 6  FIG. 7  FIG. 8  FIG. 9

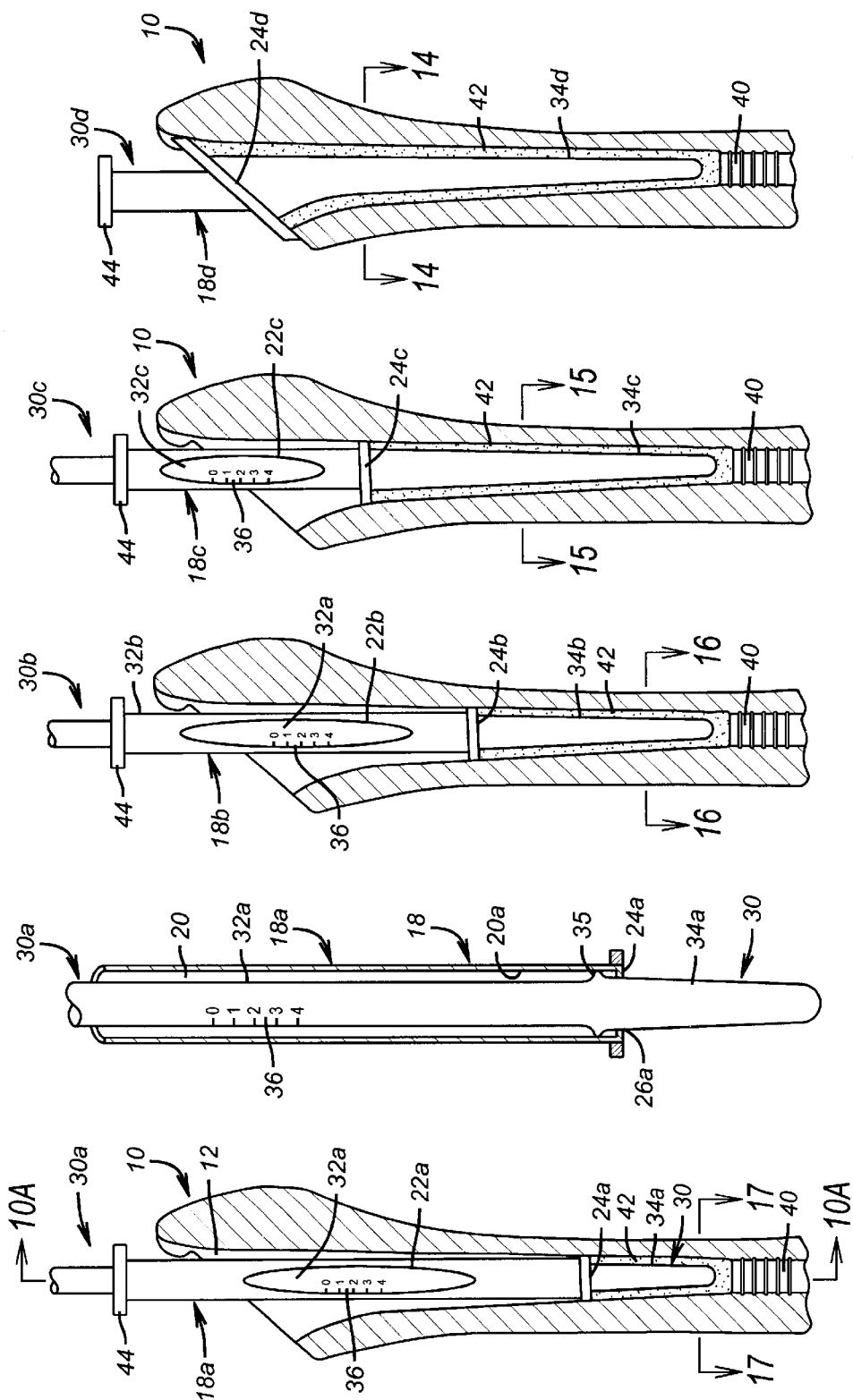

APPARATUS FOR, AND METHOD OF, PROVIDING HIP PROSTHESIS IMPLANTATION

This invention relates to apparatus for, and methods of, providing a hip prosthesis. More particularly, the invention relates to apparatus for, and methods of, providing a hip prosthesis with optimal stability over extended periods of time.

BACKGROUND

Failure of femoral components is a recognized concern. Such hip failures have occurred for a number of different reasons. For example, individuals have suffered hip failures from awkward falls and particularly falls as a result of advancing age. Until relatively recently, individuals suffering hip failures have often been unable to walk and have often been confined to wheelchairs.

In recent years, apparatus has been developed, and techniques have been developed and refined, for implanting hip prostheses. Such apparatus and techniques have involved the insertion of a prosthesis in a cavity in a patient's femur and the bonding of the prosthesis to the femur. To improve bone quality and long term prosthesis fixation, bone particles have been inserted into the cavity and a binder has been disposed between the particles and the prosthesis in an attempt to unify them.

The hip prostheses of the prior art have been far from uniformly successful. For example, as many as ten percent (10%) of the hip prostheses have had to be repeated more than once because previous prostheses have not been successful. The failures in the hip prostheses have occurred for various reasons. One primary reason has been that the bone fragments have not been tightly packed in the femur cavity which receives the prosthesis. This has created voids in the cavity. The voids cause the bone cement to be unsupported and to crack when a force is exerted by the patient on the prosthesis as by standing, walking or running.

U.S. Pat. No. 5,192,283 issued to Robin J. M. Ling, Graham A. Gie, W. E. Michael Mikhail, James M. Elting and Tom J. J. II. Sloof on Mar. 9, 1993, for a "System For Performing Hip Prosthesis Revision Surgery" is typical of the recent prior art. It involves problems which have caused failures in hip prostheses. One problem has been that the bone fragments have not been tightly packed in the cavity in the femur. This has created voids which constitute positions of weakness where failures in the prostheses have occurred.

Apparatus for, and methods of, preparing hip prosthesis implantation overcome the difficulties indicated above by packing the bone fragments tightly and substantially uniformly in a cavity in a patient's femur. Such apparatus and methods have been disclosed and claimed in U.S. Pat. No. 5,910,172 issued to me on Jan. 8, 1999, for "Apparatus For, and Method of, Preparing Hip Prosthesis Implantation." The apparatus and methods disclosed and claimed in U.S. Pat. No. 5,910,172 then cause the bone fragments to become bonded to one another and to the femur when a binder is disposed between the prosthesis and the bone fragments close to the femur. As a result, forces applied to the femur become distributed substantially uniformly throughout the femur, the prosthesis and the bone fragments. Since these forces are substantially uniformly distributed throughout the femur cavity, the forces at such positions will be below those which produce failures in the prosthesis.

In one embodiment of the invention disclosed and claimed in U.S. Pat. No. 5,910,172, each tamp in a sequence has a collar at a progressively increased distance from the bottom of a cavity in a femur relative to other tamps in the sequence. The collar on each tamp has progressively increased dimensions relative to collars on other tamps to provide a snug fit of such collar against inner walls defining the femur cavity. Bone particles are also disposed in such cavity.

After the insertion of each tamp into the cavity, such tamp is driven into the cavity to pack the bone fragments in the cavity against one another, the collar and the femur inner walls. Such tamp is then removed from the cavity and the next tamp in the sequence is inserted, and driven, into the cavity. The distance for driving each tamp into the cavity may be defined by a coincidence between a marking on such tamp and the top of the femur.

When the last tamp in the sequence is removed from the cavity, the prosthesis is inserted into the cavity. The cavity is then filled with a binder which permeates the space between the bone particles through only a limited distance because of the tight packing of the bone particles. The prosthesis is slightly narrower than the last tamp so that a thin layer of the binder is formed between the prosthesis and the bone fragments. The binder hardens against the prosthesis and the bone particles to retain the prosthesis fixedly in the cavity.

BRIEF DESCRIPTION

This invention provides an improvement over the apparatus and method disclosed and claimed in the '172 patent. The apparatus and method of this invention provide for an enhanced centralizing of the prosthesis in the femur cavity in which the prosthesis is disposed. In this way, the ability of the femur to withstand forces applied to the femur is enhanced. This substantially increases the time in which the prosthesis remains substantially implanted in the femur.

In a preferred embodiment of the invention, surface irregularities are removed from the inner wall of a femur cavity, preferably tapered. A tamp having an opening and a socket (with a particular configuration at the bottom end of the opening) is disposed in the femur cavity. The tamp may be one of a plurality of tamps each having a different length for the opening.

A guide, one of a plurality, disposed in the tamp opening has the particular configuration at an intermediate position to fits snugly in the opening. The guide has a collar which cooperates with the tamp socket to limit the movement of the guide into the tamp. A working portion of each guide below the collar has a bulbous shape which is tapered in accordance with the femur taper. Bone fragments between the guide working portion and the femur inner wall are packed against the inner wall when the tamp, and the guide movable with the tamp, are driven into the femur cavity. Numerals on the guide adjacent a slot in the tamp indicate the disposition of the guide in the tamp. Guides with working portions of progressively increasing lengths are disposed sequentially in progressive ones of the tamps to pack bone fragments at progressively increasing heights in the femur cavity against the cavity inner wall.

When the last one of the tamps and the last one of the guides have been removed from the cavity, a prosthesis having dimensions slightly less than the femur cavity dimensions is disposed in the cavity. A binder disposed in the cavity in the space between the inner wall of the femur cavity and the prosthesis binds the prosthesis to the femur.

In one embodiment, the tamp socket is an opening and the guide collar fits into the tamp opening to limit the movement of the guide into the tamp. In a modification, the tamp socket is disposed in a press fit on the guide collar to limit the movement of the guide into the tamp.

BRIEF DESCRIPTION OF THE DRAWINGS

In the drawings:

FIG. 4 is an enlarged fragmentary schematic elevational view of the guide shown in FIG. 3;

FIG. 5 is an enlarged schematic elevational view of a prosthesis which is inserted into the cavity in the femur, the prosthesis having substantially the same shape as the guide shown in FIG. 4;

FIGS. 6, 7, 8 and 9 are sectional views and are respectively taken substantially on the lines 6—6, 7—7, 8—8 and 9—9 of FIGS. 4 and 5;

FIG. 10 is a schematic elevational view, partially in section, of the femur and the femur cavity and of a first tamp disposed in the femur cavity and of a first guide disposed in the first tamp and having a working portion extending below the tamp for packing bone fragments between the cavity wall in the femur cavity and the guide working portion;

FIG. 10A is a sectional view taken substantially on the line 10A–10A of FIG. 10 and shows the tamp and the guide in additional detail;

FIG. 11 is an elevational view similar to that shown in FIG. 10 but shows a tamp of a reduced length compared to that shown in FIG. 10 and shows a guide of the same length as that shown in FIG. 10 but with a shorter portion above the tamp, and a longer working portion below the tamp, than that shown in FIG. 10;

FIG. 12 is an elevational view similar to that shown in FIG. 11 but shows a tamp of a reduced length compared to that shown in FIG. 11 and shows a guide of the same length as that shown in FIG. 11 but with a shorter portion above the tamp, and a longer working portion below the tamp, than that shown in FIG. 11;

FIG. 12A is an elevational view similar to that shown in FIG. 12 but does not include a tamp and shows a guide of the same length as that shown in FIG. 12 but with a shorter portion above the tamp, and a longer working portion below the tamp, than that shown in FIG. 12;

DETAILED DESCRIPTION

Figure 1:
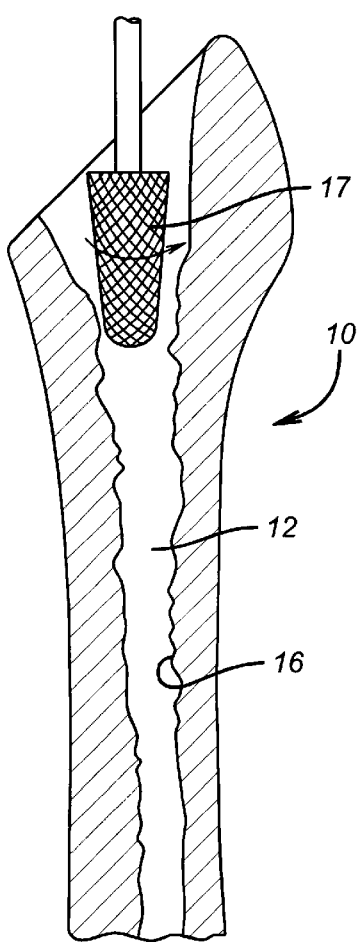
FIG. 1 is a schematic sectional view in elevation of a femur in a hip and of apparatus for producing in the femur a cavity defined by smooth walls.
Figure 2:
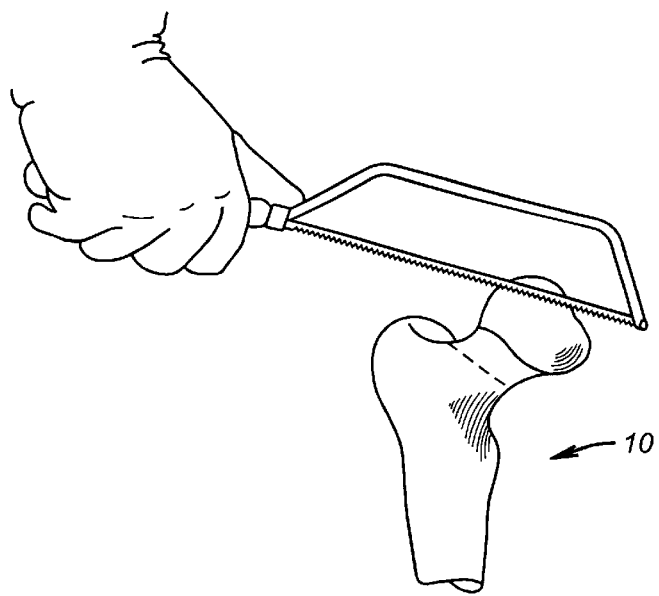
FIG. 2 is a schematic perspective view of apparatus for removing a portion of the bone at the top of the femur.
Figure 13:
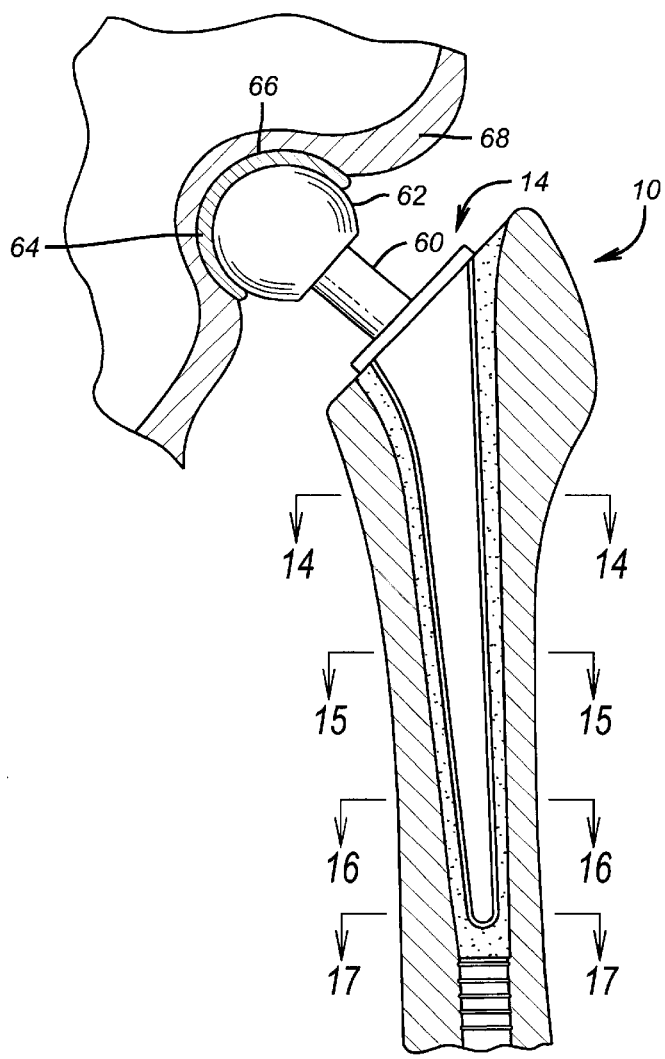
FIG. 13 is an enlarged fragmentary elevational view showing the prosthesis of FIG. 5 in the femur cavity and showing the coupling of the prosthesis to a hip bone.
Figure 14:
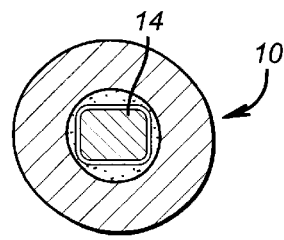
FIGS. 14, 15, 16 and 17 are sectional views respectively taken substantially on the lines 14—14, 15—15, 16—16 and 17—17 of FIG. 13 and of FIGS. 12A, 12, 11 and 10 and showing the disposition at various positions in the femur cavity of the working portion of the guide below the tamp at various positions in the femur cavity.
Figure 15:
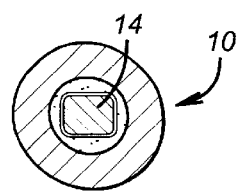
Figure 16:
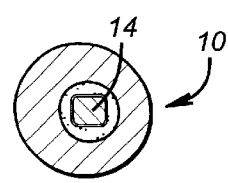
Figure 17:
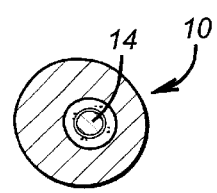

In one embodiment of the invention, a femur generally indicated at 10 (FIGS. 1, 2, 10–13) is provided. The femur is provided with a cavity 12 for receiving a prosthesis generally indicated at 14 (FIGS. 5, 13). The cavity 12 may be formed to decrease progressively in width with progressive distances downwardly in the cavity. As a first step, surface irregularities in an inner wall 16 (FIG. 1) defining the cavity 12 are removed as by disposing and rotating a rasp 17. A portion of the femur 10 may then be removed as indicated schematically in FIG. 2. This may occur before or after the surface irregularities in the femur cavity 12 are removed as shown in FIG. 1.

A tamp generally indicated.at 18 (FIG. 10A) is then disposed in the cavity 12. The tamp 18 is provided with an opening 20 which extends downwardly in substantially the same direction as the cavity 12. A slot 22 extends downwardly in the tamp 18 and communicates with the opening 20. The tamp 18 has a bottom wall 24. A socket 26 is disposed in the bottom wall 24 and preferably is provided with a configuration corresponding substantially to the configuration of the cavity 12 at a horizontal plane in the cavity corresponding to the position of the bottom wall 24.

Actually, a plurality of tamps 18a, 18b, 18c and 18d (FIGS. 10–13) may be provided. Although four (4) tamps 18a–18d are specified, it will be appreciated that any number of tamps may be provided. Each of the tamps may be provided with a different length and may be respectively provided with a bottom wall e.g. (24a, 24b, 24c 24d) corresponding to the bottom wall 24. Each of the bottom walls 24 may have a socket (e.g., 26a, 26b, 26c, 26d) corresponding to the socket 26. The dimensions of the socket depend upon the depth of the bottom wall 24 in the femur cavity 12. Thus, the tamps 18a, 18b, 18c and 18d may respectively have bottom walls 24a, 24b, 24c and 24d with sockets 26a, 26b, 26c and 26d. The tamps 18a, 18b and 18c also respectively have slots 22a, 22b and 22c corresponding to the slot 22. A similar slot is provided in the tamp 18d.

A guide generally indicated at 30 (FIGS. 10–14) is disposed in the opening 20 in the tamp 18. The guide 30 is provided at its upper end with a positioning portion 32 which is adapted to sit in the opening 20 in the tamp 18 above the bottom wall 24 of the tamp. The guide 30 also has a working portion 34 which preferably has a bulbous configuration. The working portion 34 of the guide 30 is disposed below the bottom wall 24 of the tamp 18. The bottom of the positioning portion 32 is adapted to have substantially the same configuration as the socket 26 in the tamp 18 to fit in the socket. This fitting may constitute a pressed fit. Alternatively and/or in addition, the positioning portion 32 may have slightly larger dimensions than the socket 26 so as to form a collar 35 which is retained by the socket with the working portion 34 disposed below the socket. The working portion 34 below the socket 26 also has substantially the same configuration as the socket but preferably tapers with progressive positions downwardly from the socket. Preferably, the taper in the working portion 34 substantially matches the taper in the cavity 12 in the femur 10. The guide 30 also has a plurality of indications 36 on its outer surface at progressive positions downwardly on the guide. The indications 36 are disposed relative to the slot 22 so as to be visible through the slot.

Actually, a plurality of guides 30a, 30b, 30c and 30d (FIGS. 10–14) may be provided, each associated respectively with an individual one of the tamps 18a, 18b, 18c and 18d. The number of the guides 30 may correspond to the number of the tamps 18. For example, each guide is paired with an individual one of the tamps. The pairings may respectively comprise the tamp 18a and the tamp 30a, the tamp 18b and the guide 30b, the tamp 18c and the guide 30c, and the tamp 18d and the guide 30d. The total length of each of the guides 30a–30d may be the same but the length of the working portion 34 of each of the guides may be different from the length of the working portion of the other guides. For example, the lengths of the working portions 34a, 34b and 30c of the guides 30a, 30b and 30c may be respectively shorter than the lengths of the working portions 34b, 34c and 34d of the guides 30b, 30c and 30d. This causes the lengths of the positioning portions 32a, 32b and 32c of the guides 30a, 30b and 30c to be respectively greater than the lengths of the positioning portions 32b, 32c, and 32d of the guides 30b, 30c and 30d.

Since the femur cavity 12 tapers with progressive distances downwardly in the cavity 12 and since the working portions 34 of the guides 30 have horizontal or lateral dimensions which follow the taper of the cavity, the horizontal or lateral width of the working portion of each of the guides 30a, 30b, 30c and 30d at the positions of the sockets 26 is respectively different from horizontal or lateral width of the working portion of each of the other guides. For example, the working portions of the guides 30a, 30b and 30c respectively have maximum horizontal or lateral widths which are less than the maximum horizontal or lateral widths of the working portions of the guides 30b, 30c and 30d. Each of the guides 30a, 30b, 30c and 30d respectively has indications 36 in the vertical direction on the external surface of the positioning portion 32 of the guide. These indications are respectively visible through the slots such as the slots 22a, 22b, and 22c of the tamps 18a, 18b, and 18c.

A plug 40 (FIGS. 10–12A) may be disposed at the bottom of the cavity 12. A plurality of bone fragments or particles 42 are also disposed in the cavity 12 above the plug 40. The bone fragments 42 preferably are irregularly shaped and are preferably provided with dimensions in the order of two millimeters (2 mm) to three millimeters (3 mm). The irregular shapes of the bone fragments 42 facilitate a close packing of the bone fragments in the space between the working portion 34 of the guides 30 and the inner wall defining the femur cavity 12.

Figure 3:
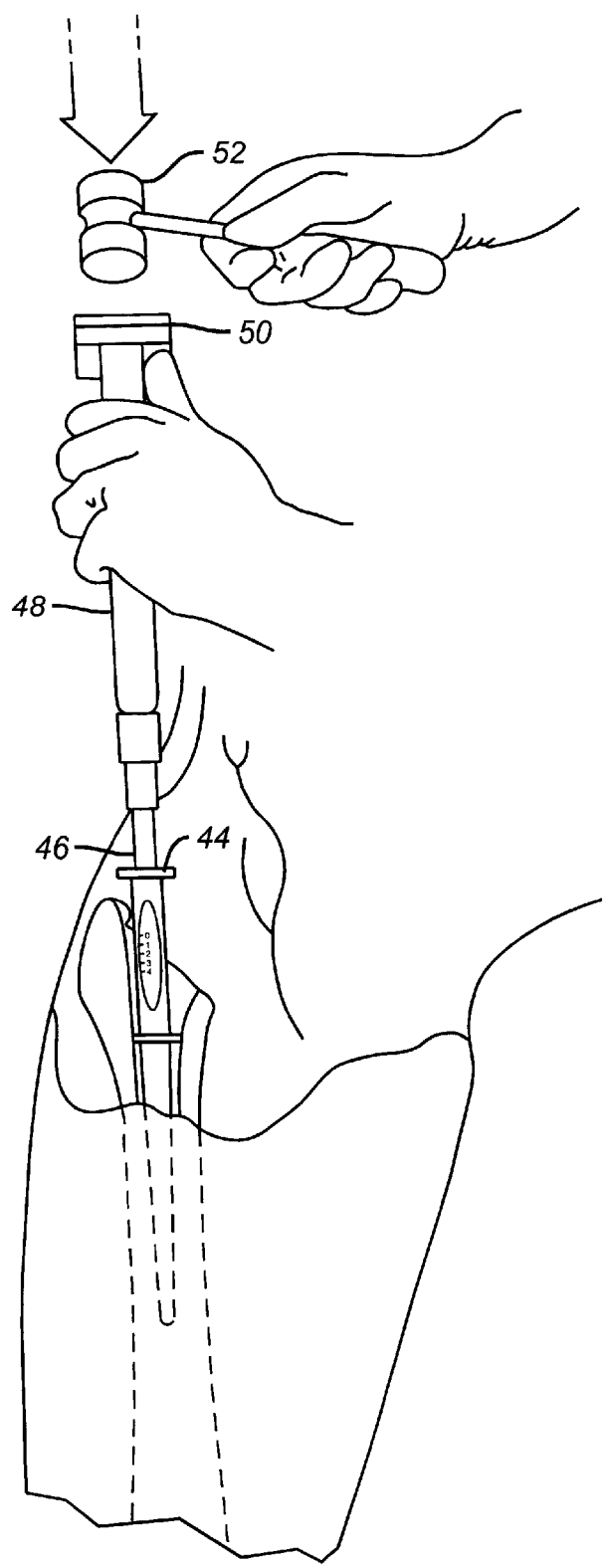
FIG. 3 is a schematic perspective view of apparatus for inserting, and driving, a tamp and a guide into the cavity in the femur.
Figure 12B:
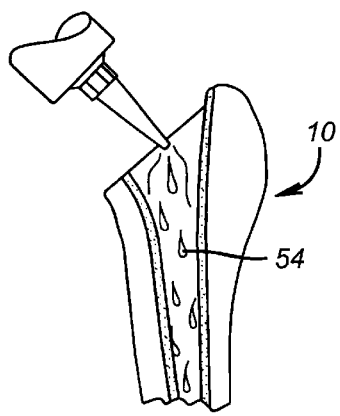
FIG. 12B is a fragmentary schematic perspective view showing the insertion of a liquid binder into the femur cavity after the removal from the cavity of a tamp and the guide shown in FIGS. 4 and 12A.

The tops of the tamps 18a–18d may be provided with a detent 44 (FIGS. 3 and 10–13) for coupling to a detent 46 (FIG. 3) on a handle 48. The handle 48 is provided with a cap 50 for receiving taps from a hammer 52 or a similar driving member to force the individual one of the tamps 18a–18d into the cavity 12. The individual ones of the tamps 18a–18d are forced progressively into the cavity 12 by applying the hammer 52 a number of successive times against the cap 50 on the handle 48. The individual one of the guides 30a–30d moves downwardly in the cavity 12 with the individual one of the tamps 18a–18d as a result of the forces applied to the tamps 18a–18d. This results from the fact that the bottom of the individual one of the positioning portions 32a–32d fits snugly in the individual one of the sockets 26a–26d and has dimensions slightly greater than the dimensions of the socket, thereby causing the tamp to drive the guide downwardly in accordance with the downward movement of the tamp.

As a first step, the cavity 12 may be initially formed in the femur 10 and the rasp 17 (FIG. 1) may be rotated in the cavity to smooth the wall defining the cavity. The bone fragments 42 may then be disposed in the cavity. The tamp 18a may then be inserted into the cavity 12. The guide 30a may be inserted into the opening 20a in the tamp with the detent 46 on the handle 48 coupled to the detent 44 on the tamp 18a. The tamp 18a and the guide 30a are then driven progressively into the cavity 12 by applying successive driving forces (as by the hammer 52) to the cap 50 on the handle 48.

The progressive movements of the tamp 18a and the guide 30a into the cavity 12 continue until the indications 36 on the guide 30a have a particular disposition in the slot 22a in the tamp 18a. When this occurs, the bone fragments or particles 42 are tightly packed by the working portion 34a of the guide 30a so as to be in engagement with one another against the guide and the inner wall defining the cavity 12. The tight packing of the bone fragments or particles 42 occurs in horizontal and vertical directions. The horizontal and vertical directions may be considered as respectively equivalent to radial and axial directions. This is shown schematically in FIG. 10. This tight packing of the bone fragments or particles 42 causes blood and tissue fluids to be squeezed from the cavity 12.

The guide 30a is then withdrawn from the opening 20a in the tamp 18a and the tamp is withdrawn from the femur cavity 12. The bone fragments or particles 42 remain tightly packed against one another and against the inner wall of the femur cavity 12 even after the guide 30a and the tamp 18a are withdrawn from the femur cavity 12. This results in part from the fact that the bone fragments or particles 42 have irregular shapes so that the tight packing of these bone fragments or particles in the horizontal and vertical directions causes the fragments or particles to be tightly intercoupled. The tamp 18a is then withdrawn from the cavity 12. Alternatively, the tamp 18a and the guide 30a may be simultaneously withdrawn from the femur cavity 12.

The tamp 18b is now inserted into the cavity 12 and the guide 30b is inserted into the opening 20b in the tamp. The steps discussed in the last three (3) paragraphs are repeated to pack the bone fragments or particles 42 tightly against one another in the horizontal and vertical directions and against the working portion 34b of the guide 30b and the walls defining the cavity 12 in the femur 10. The bone fragments or particles 42 become tightly packed in part because the working portion 34b of the guide 30b substantially abuts the inner wall defined by the cavity 12 in the femur 10 when the particular ones of the indications 36b on the guide 30b are visible in the slot 22b in the guide member 18b. As will be seen, however, the cumulative height of the tightly packed bone fragments or particles 42 in the cavity 12 after the use of the guide 30b and the tamp 18b is greater than the height of the tightly packed bone fragments 42 in the cavity 12 after the use of the guide 30a and the tamp 18a.

The tamp 18b and the guide 30b are now withdrawn from the cavity 12. Even after the withdrawal of the tamp 18b and the guide 30b from the cavity 12, the shape and the dimensions of the cavity 12 are preserved because of the tight packing of the bone fragments and particles 42 in the cavity. The tamp 18c is then inserted into the femur cavity 12 and the guide 30c is inserted into the opening 20c in the tamp. The tamp member 18c and the guide 30c are then driven into the cavity 12 until the particular ones of the indications 36c appear in the slot 22c in the tamp 18c. The bone fragments or particles 42 are packed by the working portion 34c to a height in the cavity 12 greater than the height which is produced when the bone fragments or particles are packed by the working portion 34b of the guide 30b.

The process described above is repeated for the tamp 18d and the guide 30d. After the bone fragments or particles 42 have been packed by the guide 30d, the bone fragments or particles are packed to the top of the cavity assuming that only four (4) tamps and four (4) guides are required. After the tamp 18d and the guide 30d have been withdrawn from the femur cavity 12, a suitable fluid binder 54 (FIG. 12B) such as a polymethyl methacrylate bone cement is inserted into the cavity 12. For example, a suitable binder may be obtained from Howmedica of East Rutherford, N.J. and from Zimmer of Warsaw, Ind.

The binder 54 permeates through a relatively short horizontal distance into the spaces between the tightly packed fragments or particles 42 and between the bone fragments or particles 42 and the femur 10. This permeation of the binder 54 through only a relative short distance between the bone fragments or particles 42 results from the tight packing of the bone fragments or particles. It also results from the fact that only a limited amount of the binder 54 is inserted into the cavity 12. When solidified, the binder 54 facilitates the retention of the bone fragments or particles 42 in fixed position in the femur 10.

The prosthesis 14 is then inserted into the femur cavity 12 while the binder is still in a fluid form. The prosthesis 14 may be made from a suitable material such as a stainless steel or an alloy of cobalt and chromium. Such an alloy is well known in the prior art. The prosthesis 14 has a shape corresponding substantially to the shape of the working portion 34d of the guide 30d. This may be seen from a comparison of the guide 30d in FIG. 4 and the prosthesis 14 in FIG. 5 and from the sections in FIGS. 6–9 of both the guide and the prosthesis. When the binder 54 has partially solidified after a suitable period of time such as approximately fifteen (15) minutes, the prosthesis 14 is implanted with stability in the bone fragments or particles 42 relative to the femur 10.

Actually, the width of the prosthesis 14 may be preferably slightly less than the width of the guide 30d at progressive positions in the cavity 12. This causes a layer of the binder 54 to be disposed between the prosthesis 14 and the bone fragments or particles 42. This layer may have a thickness of a few millimeters. The layer additionally permeates into the bone fragments or particles 42 for a limited distance such as a few millimeters. This permeation distance is limited because of the tight packing of the bone fragments or particles 42.

FIG. 13 schematically illustrates the hip prosthesis 14 after the hip prosthesis operation has been completed. As shown, the hip prosthesis 14 includes a stem 60 which extends upwardly from the top of the prosthesis and supports a substantially spherical member 62. A hemispherical coupling member 64 is disposed in a hemispherical socket 66 in a hip socket 68.

The prosthesis 14, the solidified bone fragments or particles 42 and the femur 10 are able to withstand large forces applied to the femur. This results from the fact that the forces are minimized at each position because of the substantially uniform distribution of forces through a large volume as a result of the tight and substantially uniform packing of the bone fragments or particles 42. This tight packing of the bone fragments or particles 42 causes the pressure exerted at each position to be relatively low even when the patient receiving the hip prosthesis is walking or running.

The disposition of the tamps 18 in the cavity 12 and the disposition of the guides 30 in the openings 22 in the tamps 18 also offer additional advantages. They provide for a centering of the working portions 34 of the guides 30 in the femur cavity 12. This enhances the ability of the prosthesis 14 to withstand forces applied to the prosthesis without becoming loosened in position in the femur cavity 12. This in turn causes the effective life of the prosthesis 14 to become significantly enhanced. The tamps 18 also tamp the bone fragments or particles 42 in he cavity 12. They also establish the depths of insertion of the guides 30 into the cavity 12. They also provide for the insertion into the cavity 12 of guides 30 with different thicknesses or widths of the working portions 34 of the guides.

It will be appreciated that deviations can be made from the features discussed above without departing from the scope of the invention. For example, the sockets 22a–22d in the tamps 18a–18d can be provided with a variety of shapes including oval, egg-shaped, square with rounded corners, rectangular with rounded corners and trapezoidal with rounded corners. Furthermore, the sections of the prosthesis 14 can be provided with different shapes as schematically illustrated in FIGS. 14–17. Furthermore, although the prosthesis 14 is shown as having a collar 70 at the top of the prosthesis, it will be appreciated that the prosthesis does not have to include the collar. In addition, the openings 22a–22d can be straight in the vertical direction rather than tapered in the vertical direction. Furthermore, a collar 70 in FIG. 5 can be provided on the prosthesis 14 but the inclusion of this collar is discretionary.

Figure 18:
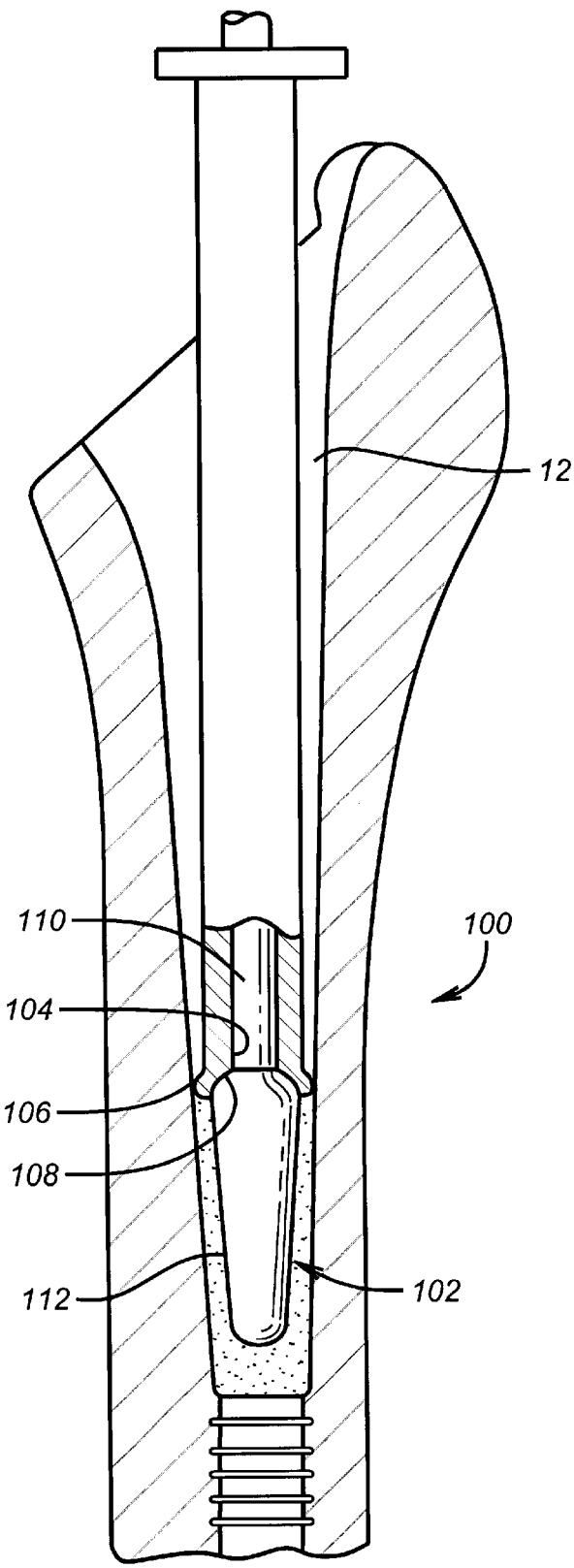
FIG. 18 is a fragmentary view, partially in section, showing a modification of a coupling of a tamp to a guide for producing a force on the tamp to position the guide at a desired position in a femur cavity.

FIG. 18 is an enlarged fragmentary sectional view of a modified tamp, generally indicated at 100, and a modified guide, generally indicated at 102. The modified tamp 100 is hollow as at 104 and includes a socket 106 at its bottom end. The hollow socket 106 preferably has a substantially constant inner diameter and fits tightly, as in a press fit, on a collar 108 of the guide 102. The collar 108 is disposed between a positioning portion 110 and a working portion 112 respectively corresponding to the positioning portion 32 and the working portion 34 of the guide 30.

It will be appreciated that the tamp 100 is only one of a plurality of tamps and that the guide 102 is only one of the a plurality of guides. Each of the tamps 100 may have a socket 106 of a different size to provide a push fit with a collar 108 of an individual size in an associated one of the guides 102. This corresponds to the sizes of the different sockets 26 in the individual one of the tamps 18 and to the sizes of the different collars 35 in the individual ones of the guides 30.

When it is desired to position the working portion 112 in the femur cavity 12, the socket 106 on the tamp 100 is push fit on the collar 108 of the guide 102. The tamp 100 is then driven downwardly into the femur cavity. Since the socket 106 of the tamp 100 and the collar 108 have a push fit relationship, the guide 102 moves downwardly in the femur cavity 12 with the tamp 100. In this way, the femur cavity 12 is progressively shaped to the desired configuration by progressive combinations of the tamp 100 and the guide 102. The prosthesis 14 is then inserted into the femur cavity 12 and bound to the walls of the cavity as by the binder 54.

Although the invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

What is claimed:

1. Apparatus for use with a femur in a hip replacement where the femur has a hollow cavity defined by an inner wall in the femur and where bone particles are implantable in the hollow cavity in the femur, including, an elongated tamp constructed for disposition in the hollow cavity in the femur, the tamp having an opening extending in the direction of the hollow cavity in the femur and having a socket near the bottom of the opening in the tamp, and an elongated guide disposed in the opening in the tamp, the guide having a collar at an intermediate position along the length of the guide, the collar extending outwardly from the guide in a direction transverse to the direction of elongation of the guide and being dimensioned for disposition in the socket near the bottom of the tamp to provide for a packing of the bone particles in the femur in the space in the cavity below the socket in the tamp between the guide and the cavity.

2. Apparatus as set forth in claim 1 wherein the tamp extends only partially into the hollow cavity in the femur in the direction of elongation of the tamp; and wherein the portion of the elongated guide below the socket in the tamp in the direction of the elongation in the guide extends further into the cavity in the femur than the tamp.

3. Apparatus as set forth in claim 1 wherein the tamp is slotted in the direction of elongation of the guide; and wherein the guide is provided with indications in the direction of the elongation of the guide at positions corresponding to the position of the slot in the tamp to indicate the displacement of the guide in the cavity in the direction of elongation of the guide.

4. Apparatus as set forth in claim 1 wherein the indications on the guide in the direction of elongation of the guide are at positions on the guide above the collar on the guide.

5. Apparatus as set forth in claim 1 wherein a handle is attached to the tamp at the upper end of the tamp and is provided with a cap at the upper end of the handle to receive forces for driving the tamp and the guide into the hollow cavity in the femur.

6. Apparatus as set forth in claim 1 wherein the tamp is one of a plurality of tamps and the guide is one of a plurality of elongated guides each shaped to extend into an associated one of the tamps in the cavity in the femur and each having a collar at an intermediate position in the direction of the elongation of the guide, the portion of the tamp below the collar in the tamp being different for each of the guides in the plurality, the collar in each of the guides extending outwardly from the guide in a direction transverse to the direction of elongation of the guide and being dimensioned for disposition in the socket in the tamp.

7. Apparatus as set forth in claim 2 wherein the tamp is slotted in the direction of elongation of the tamp and wherein the guide is provided with indications in the direction of the elongation of the guide at positions corresponding to the position of the slot in the tamp to indicate the displacement of the guide relative to the tamp in the direction of elongation of the guide and wherein the indications on the guide in the direction of elongation of the guide are at positions on the guide above the collar on the guide and wherein a handle is attached to the tamp at the upper end of the tamp and is provided with a cap at the upper end of the handle to receive forces for driving the tamp and the guide into the hollow cavity in the femur.

8. Apparatus as set forth in claim 7 wherein the tamp is one of a plurality of tamps and the guide is one of a plurality of guides each having a particular length and each shaped to extend into an individual one of the tamps and each having a collar at an intermediate position in the direction of the elongation of the guide, the portion of the guide below the collar in the guide being different for each of the guides in the plurality, the collar in each of the guides extending outwardly from the guide in a direction transverse to the direction of elongation of the guide and being dimensioned for disposition in the socket in the individual one of the tamps.

9. In a combination as set forth in claim 1 wherein the socket in the tamp fits on the collar on the guide in a push fit relationship with the collar on the guide to move the guide in accordance with the movement of the tamp.

10. In combination, a femur having a hollow cavity defined in a direction of elongation by internal walls in the femur, and bone particles disposed in the hollow cavity, an elongated tamp disposed in the hollow cavity in the femur, the tamp having an opening extending in the direction of elongation of the femur and having a socket at a particular position in the opening, and an elongated guide having characteristics for disposition in the tamp, the guide having, at an intermediate position in the guide, a collar extending outwardly in a direction transverse to the direction of elongation in the guide, the guide having a working portion which extends into the hollow cavity in the femur at positions below the collar in the guide, the collar being disposed relative to the socket in the tamp to provide for the packing of the bone fragments at progressive positions in the direction of the elongation of the working portion of the guide.

11. In a combination as set forth in claim 10, the guide constituting one of a plurality of guides, and the tamp constituting one of a plurality of tamps, each of the guides being associated with an individual one of the tamps, the working portion in each of the guides extending into the hollow cavity in the femur at positions below the associated one of the tamps, and the distance of the extension of the working portion of each of the guides into the cavity in the femur from the collar on the individual one of the tamps being different than the distance for the extension into the femur cavity of the working portions of the other ones of the guides in the plurality.

12. In a combination as set forth in claim 11, the extension of the working portion of each of the guides from the tamp into the cavity in the femur conforming substantially in shape to the shape of the cavity in the femur.

13. In a combination as set forth in claim 11 wherein the tamp has a slot which extends in the direction of the elongation of the femur and wherein indications are provided on each of the guides at positions corresponding substantially to the position of the slot in the tamp to provide for a visual indication of the disposition of the guide in the elongated direction in the cavity in the femur.

14. In a combination as set forth in claim 10, the socket on the tamp being disposed on the collar on the guide in a push fit relationship with the collar on the guide.

15. Apparatus as set forth in claim 14, including, the tamp and the guide being constructed to be driven into the cavity to pack the bone fragments below the socket against the inner wall defining the cavity in the femur.

16. Apparatus as set forth in claim 14 wherein the tamp has a detent portion at its upper end to be force driven into the cavity in the femur and to carry the guide into the cavity in accordance with the movement of the tamp into the cavity for providing a packing by the guide of the bone fragments against the inner wall of the cavity.

17. Apparatus as set forth in claim 14 wherein the portion of the guide below the socket in the tamp is bulbous to provide for a packing of the bone fragments against the wall defining the cavity in the femur.

18. Apparatus for use with a femur in a hip replacement where the femur has a hollow cavity defined as an inner wall in the femur and where bone particles are implantable in the hollow cavity in the femur, including a tamp constructed to be disposed in the hollow cavity in the femur and having an opening and a socket at a position near the bottom of the opening in the tamp, and a guide constructed to be disposed in the opening in the tamp and to be disposed in a coupled relationship with the socket in the tamp and having a working portion which extends below the socket in the tamp with a configuration dependent upon the configuration of the cavity in the femur, and a collar extending outwardly in a direction transverse to the direction of elongation in the guide.

19. Apparatus as set forth in claim 18, including, the cavity and the tamp and the guide extending in a longitudinal direction, the tamp and the guide being constructed to indicate the disposition of the guide in the tamp in the longitudinal direction of the tamp.

20. Apparatus as set forth in claim 19, including, the socket in the tamp member having a particular configuration and the portion of the guide having a collar with the particular configuration to be retained by the socket, the tamp being constructed to be driven into the cavity, the tamp having an anvil portion at its upper end to be driven by a hammer into the cavity in the femur and to carry the guide into the cavity in accordance with the movement of the tamp into the cavity for providing a packing by the guide of the bone fragments against the inner wall of the cavity.

21. Apparatus as set forth in claim 18, including, the socket in the tamp having a particular configuration and the working portion of the guide below the socket having substantially the configuration of the cavity in the femur.

22. Apparatus as set forth in claim 18, including, the socket in the tamp being hollow and being constructed to be disposed on the collar of the guide in a push fit relationship with the collar on the guide to provide a movement of the guide in the femur cavity in accordance with the movement of the tamp in the femur cavity.

23. Apparatus as set forth in claim 18, including the socket on the tamp having a female configuration and the collar on the guide having a male configuration and extending into the socket in the tamp.

\* \* \* \* \*